United States Patent [19]

Severson et al.

[11] Patent Number: 5,416,020

[45] Date of Patent: May 16, 1995

[54] LACTOBACILLUS DELBRUECKII SSP. BULGARICUS STRAIN AND FERMENTATION PROCESS FOR PRODUCING L-(+)-LACTIC ACID

[75] Inventors: David K. Severson; Cheryl L. Barrett, both of Manitowoc, Wis.

[73] Assignee: Bio-Technical Resources, Manitowoc, Wis.

[21] Appl. No.: 178,143

[22] Filed: Jan. 6, 1994

Related U.S. Application Data

[63] Continuation-in-part of Ser. No. 953,400, Sep. 29, 1992, abandoned, and a continuation-in-part of Ser. No. 953,450, Sep. 29, 1992, abandoned.

[51] Int. Cl.$^6$ .......................... C12N 1/20; C12N 1/00
[52] U.S. Cl. .................. 435/252.9; 435/139; 435/853
[58] Field of Search ...................... 435/252.9, 853, 139

[56] References Cited

U.S. PATENT DOCUMENTS

| | | | |
|---|---|---|---|
| 3,494,832 | 2/1970 | Edmond et al. | 195/48 |
| 3,818,109 | 6/1974 | Bechtle | 426/41 |
| 4,467,034 | 8/1984 | Voelskow et al. | 435/139 |
| 4,702,922 | 10/1987 | Wiesenberger et al. | 426/51 |
| 4,734,361 | 3/1988 | Murao et al. | 435/34 |
| 4,766,076 | 8/1988 | Sadine et al. | 435/253 |
| 4,771,001 | 9/1988 | Bailey et al. | 435/139 |
| 4,889,810 | 12/1989 | El-Megeed et al. | 435/252.9 |

OTHER PUBLICATIONS

Yang Lin et al, J. Nutrition, 88 (3): 323–330 (Mar., 1966).
Weinman et al, J. Bacteriology, 87(2): 263–269 (Feb., 1964).
Ragout, Pesce, Holgado & Sineriz, Presence of an L(+)-lactate dehydrogenase in cells of *Lactobacillus delbrueckii* spp. bulgaricus, *Biochimie*, 71, pp. 639–644, (1989).
Brock et al., Biology of Microorganisms, 4th Ed., Prentice-Hall, Inc.: N.J. (1984), p. 304.
Simpson et al., J. Appl. Bact., 64, pp. 299–309 (1988).
Najaraja et al., J. Vet. Res., 1985, 46(12), pp. 2444–2452.
Najaraja et al., J. Animl. Sci., 65, pp. 1064–1076 (1987).
Di Palma et al., J. Diary Sci., 70, pp. 733–737 (1987).

*Primary Examiner*—Marion C. Knode
*Assistant Examiner*—Marie L. Osoteo

[57] ABSTRACT

*Lactobacillus delbrueckii* sub-species *bulgaricus* ATCC-55163, a strain of *Lactobacillus delbrueckii* sub-species *bulgaricus* that can produce essentially stereoisometrically pure L-(+)-lactic acid, and a process for producing essentially stereoisometrically pure L-(+)-lactic acid using the strain are disclosed. A method for producing a mutant strain of Lactobacillus that produces essentially stereoisometrically pure lactic acid is also disclosed.

1 Claim, No Drawings

LACTOBACILLUS DELBRUECKII SSP. BULGARICUS STRAIN AND FERMENTATION PROCESS FOR PRODUCING L-(+)-LACTIC ACID

REFERENCE TO RELATED APPLICATIONS

This application is a continuation-in-part of U.S. patent application Ser. Nos. 07/953,400 and 07/953,450, both filed Sep. 29, 1992, and now abandoned, each of which is incorporated herein by reference.

FIELD OF THE INVENTION

The invention relates to a mutant strain of *Lactobacillus delbrueckii* subspecies *bulgaricus* ATCC-55163 and a fermentation process to produce L-(+)-lactic acid in high yield from whey, whey permeate and yeast extract.

BACKGROUND OF THE INVENTION

Lactic acid (2-hydroxypropanoic acid, 2-hydroxypropionic acid) is an organic hydroxy acid whose occurrence is widespread. It was first produced commercially in the United States in 1881 and has been in continuous production here since 1894. Concentrated whey has been used as a feedstock for producing lactic acid in the United States since 1936.

Lactic acid has two stereoisomeric forms: L-(+)-lactic acid and D-(−)-lactic acid. For certain applications, such as production of poly(lactic acid) and other lactic acid polymers, stereoisometrically pure lactic acid is required. Present commercial fermentation processes produce a mixture of stereoisomers. Since the stereoisomers are very difficult to separate, a need exists for an inexpensive fermentation process for producing a single stereoisomer of lactic acid.

SUMMARY OF THE INVENTION

The invention is a strain of *Lactobacillus delbrueckii* sub-species *bulgaricus* that can produce essentially stereoisometrically pure L-(+)-lactic acid. In another aspect the invention is a process for producing essentially stereoisometrically pure L-(+)-lactic acid. In still another aspect the invention is a method for producing mutant strains of Lactobacillus that are capable of producing essentially stereoisometrically pure lactic acid.

DETAILED DESCRIPTION OF THE INVENTION

L-(+)-Lactic Acid Production

The invention is a process for the production of L-(+)-lactic acid from whey permeate, whey and yeast extract in the presence of divalent manganese at pH 5.2 to 6.6, a temperature 38°–48° C. using a mutant strain of *Lactobacillus delbrueckii* subspecies *bulgaricus* that is capable of producing essentially 100% L-(+)-lactic acid.

The invention involves growing a mutant strain of *Lactobacillus delbrueckii* sub-species *bulgaricus* ATCC-55163 in a medium comprising 60–80 g/L whey permeate, 20–40 g/L whey, 1–6 g/L yeast extract and 5–100 ppm divalent manganese ions (calculated as MgSO$_4$) at a pH of 5.4–6.6 and a temperature of 38°–48° C.

Whey permeate is used for the growth substrate because it is a readily available by-product of the cheese and whey processing industry. Typically, the fermenter broth contains from 60–80 g/L of whey permeate, preferably 65–75 g/L. Typically the whey permeate contains 75–80 wt % lactose. Because whey permeate has had the large protein molecules removed, it is deficient in amino nitrogen, an essential nutrient for the microorganism. Therefore, conventional whey (whey solids) is added to the broth, typically 20–40 g/L, preferably 25–35 g/L. The whey normally contains from 65–75 wt % lactose. Yeast extract, typically 1–6 g/L, preferably 2–4 g/L, is also present in the fermenter broth. The yeast extract provides nutrients to the fermenter broth that are inadequately supplied by the whey permeate and whey.

Soy flour can be used to supply the nutrients supplied by whey and yeast extract. When soy flour is used, the broth typically contains 80–150 g/L of whey permeate, preferably 100–130 g/L and 2–40 g/L of soy flour, preferably 5–20 g/L.

The addition of divalent manganese ions to the fermenter broth has been found to dramatically increase the rate of lactic acid production without affecting the ratio of L-lactic acid to D-lactic acid being produced. Generally the manganese needs to be present at a level of at least 5 ppm. Above about 100 ppm the manganese slows growth of the microorganisms. The divalent manganese can be present in the form of any soluble salt that does not affect growth of the microorganism. Suitable salts include, for example, sulfate, chloride, etc.

The amount of L-lactic acid produced is essentially 100% through the pH range 5.4–6.6, the pH range suitable for lactic acid production. The preferred pH range for lactic acid production is 5.6–6.2. Any suitable base such as ammonium hydroxide, sodium hydroxide, etc., can be used for pH control.

Generally, the microorganism can be grown up to about 75 g/L lactic acid. The growth rate is faster at concentrations below about 40 g/L lactic acid.

Lactic acid can be isolated by any of a number of conventional techniques, such as membrane separation, ion exchange, solvent extraction, electrodialysis, and precipitation of lactate salts. Cockrem, U.S. Pat. No. 5,210,296, incorporated herein by reference, discloses recovery of lactic acid from fermentation broth by: esterification of the lactic acid, preferably with an alcohol containing 4 or 5 carbon atoms, such as 1-buutanol; distillation of the resulting lactate ester; and hydrolysis of the ester to lactic acid. Other recovery processes are also discussed in this patent.

Mutant Strain Production

Suitable Lactobacillus species for use herein include, but are not limited to *Lactobacillus delbrueckii* and *Lactobacillus helveticus*. A culture of Lactobacillus can be mutagenized by any conventional method. Typical conventional methods include exposure to radiation, such as ultraviolet irradiation, or exposure to a chemical mutating agent, such as, for example, ICR 191 (an acridine-based frameshift mutagen) or ethyl methane sulfonate. These methods are well know to those skilled in the art.

Mutagenized isolates are subjected penicillin enrichment. This procedure selects isolates that produce only a single stereoisomer of lactic acid. L-Lactate and D-lactate will each inhibit their respective lactate dehydrogenase enzymes (LDH). Cell growth will be inhibited if the alternate dehydrogenase is absent. If a sufficient quantity of L-lactate is added to a mutagenized culture, those cells lacking D-lactate dehydrogenase (D-LDH) will cease to grow. Cells that contain D-LDH will continue to grow. These cells will be killed when penicillin is added, leaving only D-LDH deficient cells To inhibit cell growth, 1.0–3.0 wt. % (weight/volume) lactic acid is typically added, preferably 1.5–2.0 wt. % lactic acid.

The penicillin enrichment procedure can yield a large number of false positives, possibly due to the development of penicillin-resistant mutants. Incorporation of cycloserine (a cell wall production inhibitor) into the medium can be used to decrease the number of false positives. In several trial of this procedure employing known racemic and D-lactate-deficient strains, the D-lactate-deficient strains were selected over the racemic strains, demonstrating the validity of the procedure.

Several thousand isolates from the penicillin enrichment procedure were subjected to the primary screen. About a hundred passed and were subjected to the secondary screen. One was confirmed to be D-lactate deficient.

The mutated cultures are plated onto fast-slow differential agar that identifies isolates of high lactate productivity on a milk or whey-based medium. These higher productivity isolates are then transferred to a high-throughput liquid medium assay (primary screen) which identifies isolates which are D-lactate deficient. These isolates are then tested in an end-point assay (secondary screen) to qualify then for fermenter trials.

In the primary screen the isolates are manifested as single colonies on an agar plate. An acid-base indicator such as bromcresol purple is used to define the extent of lactic acid production. A clearing zone about each colony defines the extent of proteolytic activity, hence efficiency of substrate utilization. The diameter and height of each colony also serves as an indicator of strain viability. The procedure involves preparing serial dilutions of the mutated Lactobacillus in 0.9% saline solution, spread-plating the dilution onto the agar surface with a sterile glass spreader, and incubating the cells anaerobically using an atmosphere of 95 wt. % $N_2$ and 5 wt. % $CO_2$. The plates are then read. Single isolates are transferred aseptically to a suitable nutrient media, such as non-fat sterile milk in 10 mL tubes, for storage. In reading the plates the following criteria are used to interpret colony morphology:

| Colony Morphology | Phenotype |
|---|---|
| yellow, large, raised, clear zone | lactose+, protease+ |
| yellow, small, flat, no clear zone | lactose+, protease– |
| colorless, small flat, no clear zone | lactose–, protease+; or lactose–, protease– |

The primary screen is a D-lactate deficiency assay that operates on the principle that D-lactate plus nicotinamide adenine dinucleotide (NAD) will yield pyruvate and reduced NAD catalyst by D-lactate dehydrogenase (NADH). The NADH produced will react with phenazine methosulfate (PMS) to form NAD plus PMS (PMSH). The PMSH reduces a redox dye, iodonitrotetrazolium violet (INT) which becomes either colorless in its oxidizing form, the reduced INT forms as a red precipitate or the PMSH can react with the INT form PMS plus INTH which forms as a red precipitate. Thus, D-lactate deficient isolates cause no color change while those producing any amount of D-lactate acid will turn red. The procedure involves selecting isolates from fast-slow differential agar plates of freshly-grown mutated cells, which cells are subcultured to multi-well microtest plates containing a suitable amount of nutrient media, typically 300 μL of MRS broth per well. The cells are incubated anaerobically until visible surface growth appears, typically at 40°–42° C. for about two days.

The cultures are transferred to corresponding multi-well plates containing a smaller amount of nutrient media per well. The cells are then incubated until visible growth appears, typically at 40°–42° C. for two days. The cells are then pelleted, typically by centrifugation at 1500 rpm for 5 minutes. Then samples are transferred from each well into corresponding multi-well plates. This can be done in a non-sterile fashion. An assay reagent is added to each well and the well contents thoroughly mixed. A suitable assay reagent is 100 μL of an aqueous solution of 26.7 mM glycylglycine buffer (pH 9.2), 0.75 g/L nicotinamide adenine dinucleotide, 0.087 g/L phenazine methosulfate, 0.22 g/L iodonitrotetrazolium violet, and 14.8 μ/mL D-lactate dehydrogenase (D-LDH).

The assay trays are incubated for about 15 to 20 minutes at 38°–42° C., and viewed against a white background for color formation. The assay trays should be viewed within ten minutes following the incubation period to prevent false readings due to non-specific dye reduction. D-lactate positive isolates will exhibit a red to deep red color, while D-lactate deficient isolates will exhibit little to no color change. The D-lactate deficient isolates from the original agar-containing microtest plate are subcultured into suitable storage containers containing an aqueous solution comprising non-fat sterile milk solids. They are incubated at about 40°–42° C. until the milk coagulates and neutralized with two drops of sterile 5N aqueous sodium hydroxide. The cells are then transferred to fresh non-fat sterile milk at the 10% level, and refrigerated until needed for further screening.

INDUSTRIAL APPLICABILITY

L(+)-Lactic acid is used in the manufacture of poly(lactic acid) and copolymers of lactic acid with other α-hydroxy acids. Because these materials degraded biologically and hydrolytically to physiologically and environmentally acceptable materials, they are useful in biomedical and other applications. They are also potential replacements for poly(styrene) and other non-biodegradable polymers. The advantageous properties of this invention can be observed by reference to the following examples which illustrate, but do not limit, the invention.

EXAMPLE 1

This example illustrates the mutation of a Lactobacillus to produce a mutant strain that produces L-(+)-lactic acid.

The parent strain was identified by the supplier as *Lactobacillus bulgaricus*, strain R-160 Biolac ™ Defined Strain Starter (Marschall Products, Madison, Wis. 53701). This strain typically produces 70% L-(+)-lactic acid and 30% D-(−)-lactic acid. *Lactobacillus bulgaricus* has also been classified as *Lactobacillus delbrueckii* sub-species *bulgaricus*. The latter name is believed to be the currently accepted designation.

Samples of whey/whey permeate broth (10 mL) were inoculated with cells of the parent strain the evening before mutation and incubated at 40° C. The resulting culture was subcultured at about 0.5% (50 μL) to 10 mL whey/whey permeate to which was added about 500 μL of ICR 191 at 0.5 mg/mL (final concentration=25 μg/mL) and incubated at 40° to about 42° C.

overnight. The cells were washed by centrifugation at 2,700 rpm for 10 min, the supernatant was poured off, and the cells re-suspended in 10 mL 0.9% saline. The washing procedure was repeated.

The washed cells were subcultured to 5 mL of fresh whey/whey permeate broth at 1%. The cells were incubated for about 2-2.5 hr at 42° C. Then 15 g/L of sodium L-lactate was added aseptically and incubation was continued for about 5 hr at 42° C. Then 5,000 units/mL of penicillin G (benzylpenicillin) was added. The penicillin G was added as a solution containing 23 g/L whey permeate, 10 g/L whey solids, 6 g/L yeast extract, 15 g/L sodium L-lactate and 5,140 units/mL penicillin G. Incubation was continued overnight at 42° C. The test tube containing the cells was vortexed and the entire contents transferred to a sterile polypropylene centrifuge tube. The tube was centrifuged for 20 min at 15,000 rpm, the supernatant poured off, and the cells suspended in 0.9% saline. The cells were centrifuged at 15,000 rpm for 20 min and the supernatant poured off. The cells were re-suspended in 0.9% saline and centrifuged at 15,000 rpm for 20 min. The supernatant was poured off. The cells, re-suspended in 10 mL of 0.9% saline and 50 g/L of the suspension, were subcultured to 5 mL of fresh whey/whey permeate broth and the above steps repeated. The dilutions of the cells in 0.9% saline solution were spread-plated onto FSDA plates with a sterile glass spreader. The cells were incubated anaerobically under a 95:5 $N_2/CO_2$ gas mixture at 40°-42° C. for 48 hr. Plates with yellow, large, raised colonies surrounded by a clear zone were selected for further evaluation.

From FSDA plates of freshly-grown mutated cells, isolates were selected and subcultured to 96-well microtest plates containing 300 μL MRS broth per well. The cells were incubated anaerobically for 48 hr, at which time visible surface normally could be detected. The cultures were transferred to corresponding 96-well plates containing 250 μL MRS broth per well using a sterile 96-pin inoculator. The cells were again incubated at 40°-42° C. for 48 hr. The cells were then pelleted by centrifugation at 1,500 rpm for 5 min. Twenty-five microliters were transferred from each well using an eight-place micropipettor into corresponding non-sterile 96-well plates. One-hundred microliters of assay reagent was transferred to each well using an eight-pace micropipettor, mixing thoroughly by drawing and discharging the well contents two to three times. The micropipettor was discharged completely and the pipette tips touched off on a paper towel before proceeding to a new row. The assay reagent was an aqueous solution containing 26.7 mM glycylglycine buffer (pH 9.2) 0.75 g/L nicotinamide adenine dinucleotide, 0.087 g/L phenazine methosulfate, 0.22 g/L iodonitrotetrazolium violet, and 14.8 units/mL D-lactate dehydrogenase.

The trays were incubated for 15 min and viewed against a white background for color formation. To prevent false readings due to non-specific dye reduction, viewing was done within 10 min after the end of incubation. D-Lactate positive isolates exhibit a red to deep red color, while D-lactate deficient isolated exhibit little to no color change.

The D-lactate deficient isolates from the original agar-containing microtest plates were subcultured into 10 mL tubes containing NFS. The tubes were incubated at 40°-42° C. until the milk coagulated at which time two drops of sterile 5N aqueous sodium hydroxide was added to each tube and the cells were transferred to fresh NFS at the 10% level and the tubes were refrigerated until needed for the secondary screen.

The NFS was prepared by adding 0.5 g yeast extract (Stauffer Type KAT) to 500 mL distilled water, and mixing thoroughly with a magnetic bar. Non-fat dry milk solids (50 g) (Foremost Dairies) were slowly added to the medium, stirring the powder into the vortex adding two drops of Dow 1510 silicone defoamer. When the milk was dispersed, 10 mL was dispensed into each 10×150 mM test tubes while the medium was still being stirred to keep the solids in even suspension. The tubes were capped and autoclaved for 15 min at 15 psi and promptly removed. Allowing the tubes to remain in the autoclave for an extended cool-down period can cause excessive protein denaturation.

The isolates in 10 mL NFS, which were inoculated at 10%, as described above, and stored at 7° C. were grown at 42° C. until the milk coagulated, at which point each tube was neutralized with two drops of about 5N NaOH. The cells were subcultured to 60 mL BOD bottles containing 47.5 mL of whey/whey permeate blend at 5%. The whey/whey permeate contained 10 g/L yeast extract (Stauffer Type EAT), 4.5 g/L whey permeate solids (Northern Milk Products), 1.9 g/L whey solids (Northern Milk Products) and 5 g/L $Mg_3(PO_4)_2$. It was prepared by adding about 0.3 g $Mg_3(PO_4)_2$ to 60 mL BOD bottles, autoclaving the bottles for 15 min at 15 psi on a dry cycle. Yeast extract (10 g) was dissolved in 0.8 L distilled water. Then 5 g dry whey permeate and 2.22 g dry whey were thoroughly mixed in. Into each sterile BOD bottle 47.5 mL of the mixture was pipetted, mixing while pipetting, to assume a homogeneous broth. The bottles were pasteurized by immersing them for 0.5 hr in a water bath maintained at about 85° C. The bottles were removed from the bath, placed in a cooling water bath at ambient temperatures for about 15 min., removed from the cooling bath, and equilibrated in a water bath maintained at 42° C. for at least about 0.5 hr. A sample of the cells was subcultured at 10% to a fresh NFS tube and the culture retained at 7° C. The inoculated BOD bottles were incubated for 16 hr at 42° C. Then a 5 mL sample was taken and centrifuged at 10,000 rpm for 7 min. A 0.5 mL sample of the cells was drawn off and placed in a 2 mL vial containing 0.5 mL of 10% trichloroacetic acid. The vials were promptly frozen.

The lactic acid stereoisomer ratio produced by each isolate was determined by enzymatic essay (*Methods of Enzymatic Analysis*, Vol. 6, H. U. Bergmeyer, Ed., Verlag-Chemie, Weinheim, Germany, 1984, p. 582). A strain that produces essentially 100% L-(+)-lactic acid was isolated. This strain was deposited with the American Type Culture Collection, 12301 Parklawn Drive Rockville, Md. 20852, U.S.A., on Mar. 28, 1991, as *Lactobacillus delbrueckii* subspecies *bulgaricus* ATCC-55163.

EXAMPLE 2

This example illustrates that productivity increases, but the isomer ratio does not change, as the pH of the fermenter broth is changed from 5.4 to 6.0.

*Lactobacillus delbrueckii* sub-species *bulgaricus* ATCC-55163 was cultured at 42° C. in an aqueous medium containing 84.4 g/L whey permeate, 36.1 g/L whey solids, 3 g/L of yeast extract, and 0.014 g/L of manganese sulfate. pH was controlled by the addition of 8N ammonium hydroxide. The results are reported in Table 1.

TABLE 1

| pH | L-Isomer % | Lactic Acid g/L | Productivity g/L/hr |
|---|---|---|---|
| 5.4 | 100 | 57.9 | 1.50 |
| 6.0 | 100 | 77.7 | 2.01 |

EXAMPLE 3

This example shows how lactic acid could be produced on a large scale.

*Lactobacillus delbrueckii* sub-species *bulgaricus* ATCC-55163 is cultured in 500 mL of an aqueous medium containing 50 g sterile non-fat milk solids, 0.5 g yeast extract, 0.5 g $K_2HPO_4$ and 0.01 g $MnSO_4$ for 12 hr at 42° C. The culture is transferred to a 10 L fermenter containing a culture medium containing 70.4 g/L (dry basis) whey permeate having a lactose content of 80%, 30 g/L whey (dry basis) having a lactose content of 74%, 3 g/L yeast extract (Amberex® 695 Universal Foods) and 0.02 g/L manganese sulfate. This provides lactose at a level of about 78 g/L. The fermenter broth is maintained at 42° C. and pH 5.4 (controlled with ammonium hydroxide) for about 8 hr at which time about 35 g/L lactic acid is produced.

The fermenter broth is then transferred to a 200 L fermenter containing the same nutrient medium used in the 10 L fermenter and also maintained at 42° C. and pH 5.4. After about 8 hr the lactic acid content of the fermenter broth reaches about 35 g/L. The fermenter broth is transferred to a 6,000 L fermenter that contains the same nutrient medium used in the 10 L fermenter. The 6,000 L fermenter is maintained at 42° C. and pH 5.4 for about 8 hr at which time the fermenter broth contains about 35 g/L lactic acid.

The contents of the 6,000 L fermenter are then transferred to an 80,000 L fermenter containing the same nutrient medium used in the 10 L fermenter. The fermenter is maintained at 42° C. pH is controlled at pH 6.0 using ammonium hydroxide. After about 20 hr the lactose has been depleted and fermentation is complete at about 50 g/L lactic acid. The fermenter is drained, the cells separated, and lactic acid recovered. The lactic acid is essentially 100% L-lactic acid.

EXAMPLE 4

This example illustrates production of lactic acid using soy flour in place of the whey solids and yeast extract.

*Lactobacillus delbrueckii* sub-species *bulgaricus* ATCC-55163 was cultured at 42° C. in an aqueous medium containing 120 g/L whey permeate, 10 g/L of soy flour, and 0.014 g/L of manganese sulfate. pH was controlled at about 6.0 by the addition of 8N ammonium hydroxide. Lactic acid was produced. Concentration: 77.8 g/L. Productivity: 1.11 g/L/hr. Enzymatic analysis indicated the lactic acid was 99.6% L-(+)-lactic acid. The small amount of D-(−)-lactic acid present is believed to have been contributed by the medium.

Having described the invention, we now claim the following and their equivalents.

What is claimed is:

1. *Lactobacillus delbrueckii* sub-species *bulgaricus* ATCC-55163.

* * * * *